(12) United States Patent
Alessandri et al.

(10) Patent No.: US 9,061,170 B2
(45) Date of Patent: Jun. 23, 2015

(54) APPARATUS FOR THE ASSISTED PERFORMANCE OF A FITNESS EXERCISE

(71) Applicant: TECHNOGYM S.P.A., Gambettola (Forli Cesena) (IT)

(72) Inventors: Nerio Alessandri, Gambettola (IT); Jarno Guidi, Gambettola (IT); Flavio Venturi, Gambettola (IT)

(73) Assignee: TECHNOGYM S.P.A., Gambettola (IT)

( * ) Notice: Subject to any disclaimer, the term of this patent is extended or adjusted under 35 U.S.C. 154(b) by 0 days.

(21) Appl. No.: 14/548,941

(22) Filed: Nov. 20, 2014

(65) Prior Publication Data

US 2015/0080183 A1 Mar. 19, 2015

Related U.S. Application Data

(62) Division of application No. 13/096,472, filed on Apr. 28, 2011, now Pat. No. 8,911,328.

(30) Foreign Application Priority Data

Apr. 28, 2010 (IT) ............... BO2010A0261

(51) Int. Cl.
*A63B 71/00* (2006.01)
*A63B 15/02* (2006.01)
*A63B 24/00* (2006.01)

(52) U.S. Cl.
CPC ................... *A63B 24/0062* (2013.01)

(58) Field of Classification Search
CPC ........... A63B 24/0021; A63B 24/0062; A63B 24/0003; A63B 24/0075; A63B 2220/803; A63B 2220/806; A63B 24/00; A63B 2220/805; A63B 2220/10; A63B 2220/807; A63B 2024/0012; A63B 2024/0015
USPC .................. 482/1–9, 900–902, 909; 473/131, 473/266–277; 434/1–5
See application file for complete search history.

(56) References Cited

U.S. PATENT DOCUMENTS

| 4,830,021 A | 5/1989 | Thornton |
| 4,919,418 A * | 4/1990 | Miller ............................... 482/6 |
| 5,655,997 A * | 8/1997 | Greenberg et al. ............... 482/5 |

(Continued)

FOREIGN PATENT DOCUMENTS

| DE | 10 2006 047 099 A1 | 4/2008 |
| EP | 0336030 A1 | 10/1989 |

(Continued)

*Primary Examiner* — Oren Ginsberg
*Assistant Examiner* — Joshua Lee
(74) *Attorney, Agent, or Firm* — Pearne & Gordon LLP

(57) ABSTRACT

An apparatus for the assisted performance of a fitness exercise, equipped with a fitness tool configured to interact with the user to enable the user to perform a movement along a preset path overcoming the force of a resistant load, comprises: sensing means set up to provide a signal representing the movement of the user; feedback means for transmitting a signal to the user during performance of the exercise; a processor connected to the sensing means and to the feedback means to provide the user with feedback in real time on the correctness of performance of the exercise, based on a comparison between the signal representing the movement of the user and a predetermined reference pattern representing an ideal pattern for the movement of the user corresponding to the exercise performed correctly.

17 Claims, 7 Drawing Sheets

(56) References Cited

U.S. PATENT DOCUMENTS

| | | | |
|---|---|---|---|
| 5,846,086 A * | 12/1998 | Bizzi et al. | 434/247 |
| 6,148,280 A | 11/2000 | Kramer | |
| 6,210,301 B1 | 4/2001 | Abraham-Fuchs et al. | |
| 6,358,188 B1 * | 3/2002 | Ben-Yehuda et al. | 482/8 |
| 7,018,211 B1 | 3/2006 | Birkholzer et al. | |
| 7,455,621 B1 * | 11/2008 | Anthony | 482/8 |
| 7,666,118 B1 | 2/2010 | Anthony | |
| 7,670,270 B2 | 3/2010 | Alessandri et al. | |
| 7,794,359 B1 * | 9/2010 | Lannon et al. | 482/8 |
| 7,901,340 B2 | 3/2011 | Alessandri et al. | |
| 8,038,576 B2 * | 10/2011 | Farinelli et al. | 482/3 |
| 8,328,691 B2 | 12/2012 | Lanfermann et al. | |
| 8,435,177 B2 * | 5/2013 | Lanfermann et al. | 600/301 |
| 2003/0040348 A1 * | 2/2003 | Martens | 463/1 |
| 2003/0054327 A1 * | 3/2003 | Evensen | 434/252 |
| 2004/0072659 A1 | 4/2004 | Alessandri et al. | |
| 2004/0176226 A1 * | 9/2004 | Carlson | 482/112 |
| 2005/0070407 A1 | 3/2005 | Alessandri et al. | |
| 2007/0232452 A1 | 10/2007 | Hanoun | |
| 2009/0033770 A1 * | 2/2009 | Johnson | 348/231.99 |
| 2009/0131225 A1 | 5/2009 | Burdea et al. | |
| 2009/0233769 A1 * | 9/2009 | Pryor | 482/8 |
| 2009/0298649 A1 * | 12/2009 | Dyer et al. | 482/4 |
| 2010/0015585 A1 * | 1/2010 | Baker | 434/247 |
| 2010/0022351 A1 * | 1/2010 | Lanfermann et al. | 482/1 |
| 2010/0173276 A1 * | 7/2010 | Vasin | 434/307 R |
| 2010/0302142 A1 * | 12/2010 | French et al. | 345/156 |
| 2011/0006926 A1 * | 1/2011 | Kim et al. | 341/20 |
| 2011/0039659 A1 * | 2/2011 | Kim et al. | 482/8 |
| 2012/0283080 A1 | 11/2012 | Mayr | |

FOREIGN PATENT DOCUMENTS

| | | |
|---|---|---|
| EP | 0959956 A1 | 12/1999 |
| EP | 1402925 A1 | 3/2004 |
| EP | 1506798 A2 | 2/2005 |
| EP | 2316540 A1 | 5/2011 |
| WO | 2008000919 A1 | 1/2008 |
| WO | 2009013679 A2 | 1/2009 |

* cited by examiner

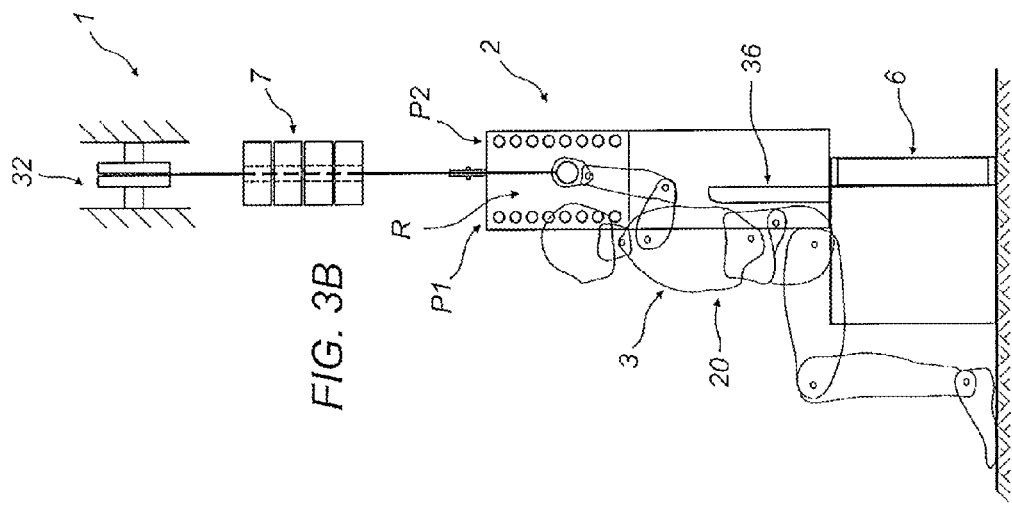
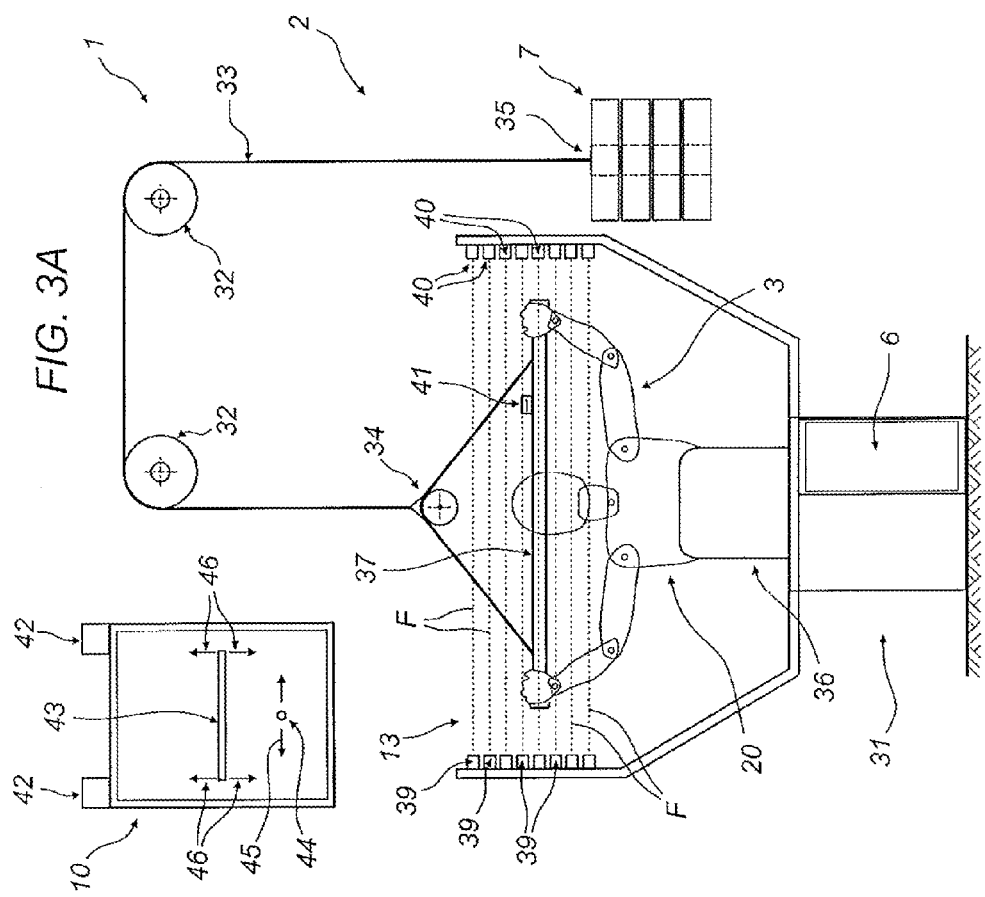

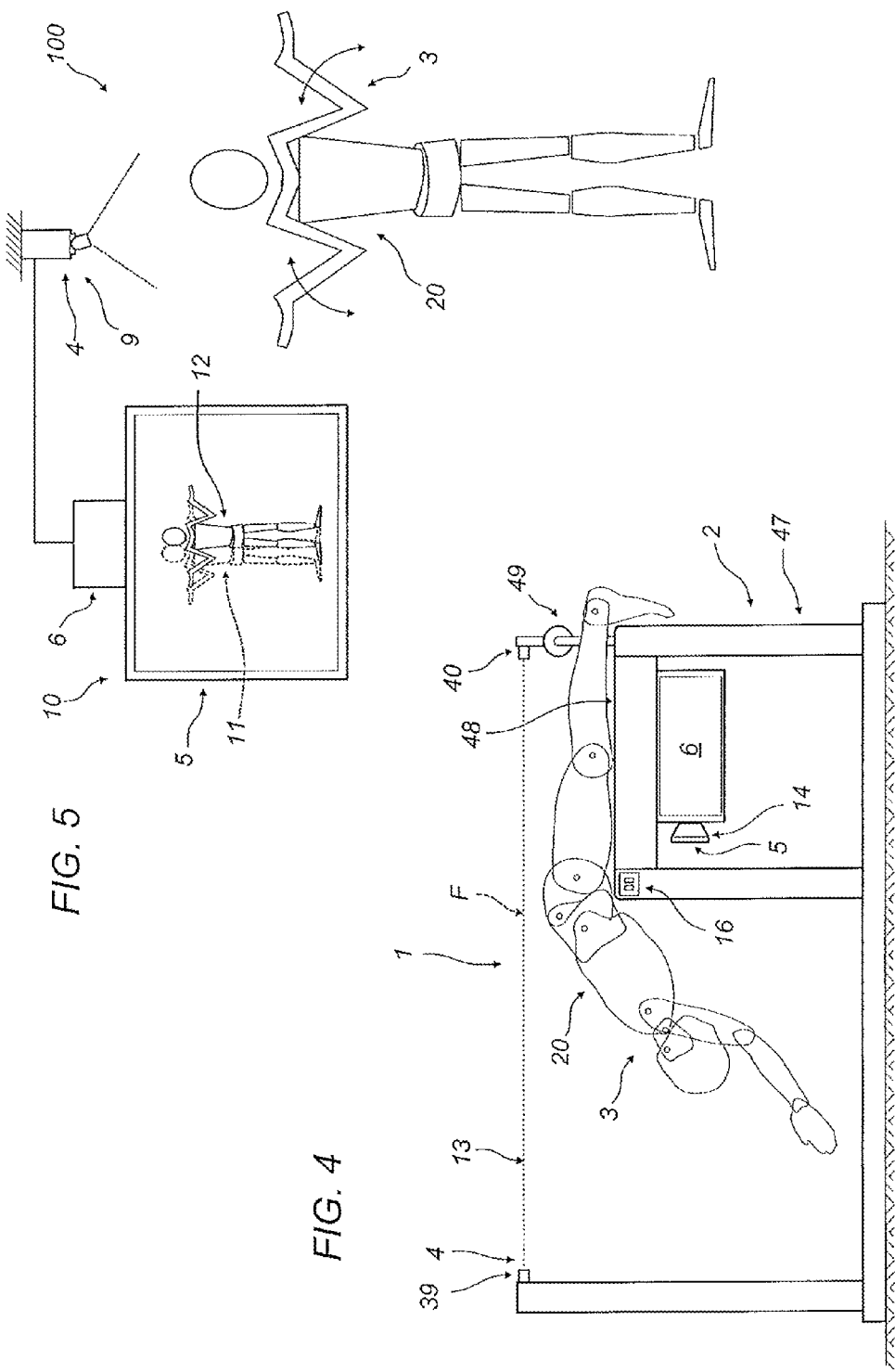

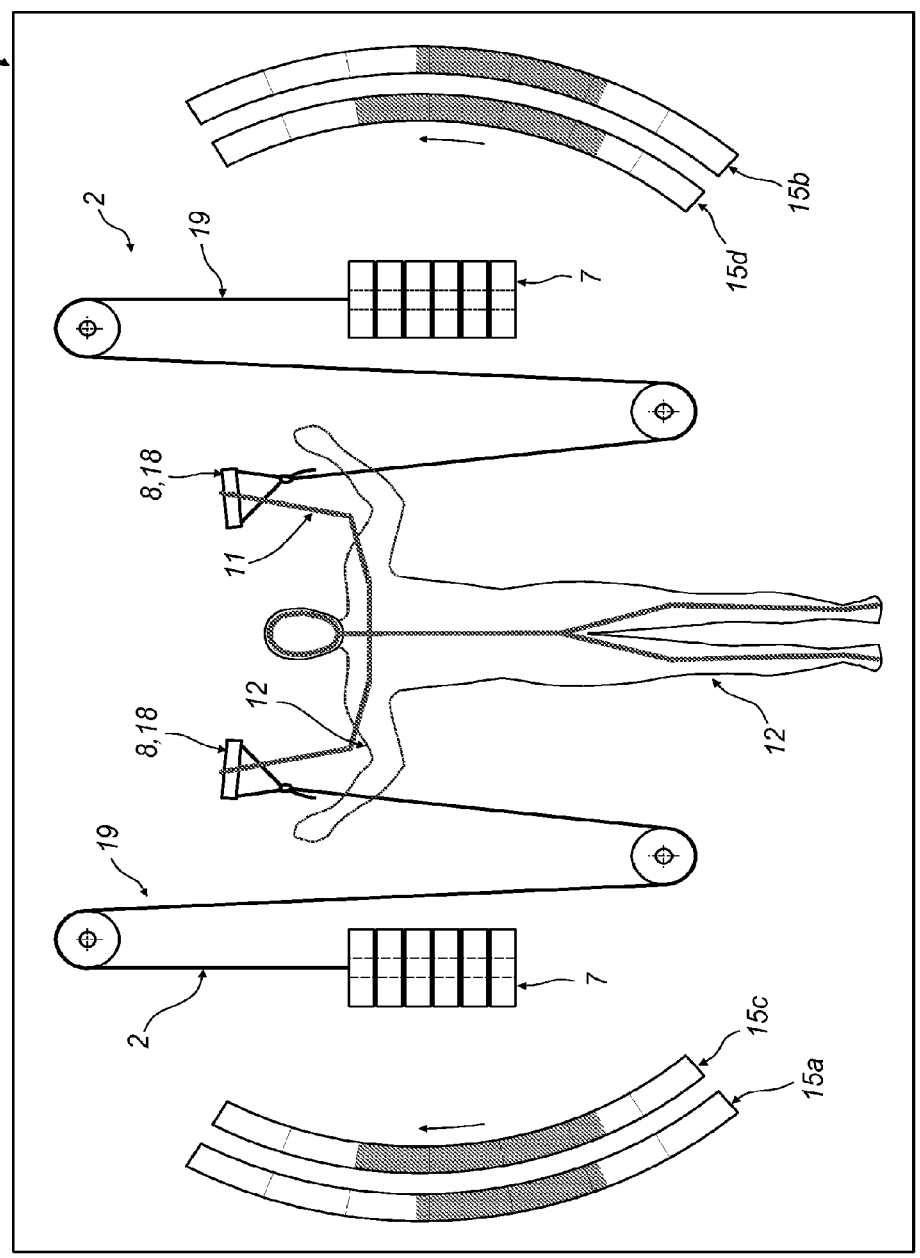

APPARATUS FOR THE ASSISTED PERFORMANCE OF A FITNESS EXERCISE

TECHNICAL FIELD

This invention relates to an apparatus and a method for the assisted performance of a fitness exercise and an apparatus for assisting the user in the performance of a free body fitness exercise.

BACKGROUND ART

Known in the prior art are fitness tools designed to allow a user to perform a fitness exercise.

Some of these tools comprise a resistant weight and a mobile element connected to the weight which allow the performance of a plurality of fitness exercises for training a plurality of human body muscles. Other tools define constraints allowing the user to train by performing predetermined movements and using the body as the resistant load.

For example, European patent EP1402925 to the same Applicant as this invention, describes an exercise machine comprising a frame, a plurality of pulleys fixed to the frame, a cable trained around the pulleys, a pair of resistant loads to which the respective ends of the cable are connected, and a mobile element in the form of a handgrip slidably associated with the cable and designed to be gripped by the user and to be moved along a path for performing a fitness exercise.

Patent document EP1506798 in the name of the same Applicant as this invention describes an exercise machine which can be used by a plurality of users at the same time.

The exercise machine comprises a plurality of exercise zones, each designed to be occupied by a user performing an exercise. In each exercise zone, there is a cable connected to a resistant load which allows the user to perform the fitness exercise.

The exercise machines described above are very versatile and allow the user to perform a plurality of different exercises for training a plurality of body muscles.

Whatever the exercise, it is essential that the user perform the exercise correctly so as to gain the most benefit from it.

In effect, performing an exercise incorrectly, besides reducing the benefits associated with that exercise (the benefit being, for example, improving muscle power and developing muscle tone), involves a risk of muscle damage and, in the long term, may lead to serious degenerative diseases of the spinal column.

Fitness establishments such as gyms normally employ trainers, that is to say, physical education specialists, responsible for supervising fitness equipment users during exercise sessions.

If a trainer believes that a user is not performing an exercise properly, he or she provides the user with instructions and explanations on how the exercise should be performed.

For economic reasons, a gym has a relatively small number of trainers compared to the number of fitness equipment users. Thus, each trainer is obliged to keep an eye on different fitness equipment users in turn, which means that the attention dedicated to supervising the exercises of any one particular user is inevitably limited.

Moreover, when not inside a gym, a user of fitness equipment very often performs exercises without any supervision.

For example, a person using a fitness tool at home usually performs an exercise without the supervision of a trainer, mainly on account of the high cost of calling a trainer to supervise an exercise session performed in the user's home.

Thus, the only supervision available to a user in most of such cases is the user's own personal discretion and experience, with the aid, for example, of a mirror placed near the exercise tool with which to visually monitor his or her own movements.

Even the benefits of a mirror, however, are limited because the user does not always possess the competence to spot the mistakes he or she is making in doing an exercise and is therefore unable to correct them. Also, the user may not even remember the proper way of performing an exercise, especially when a long time has passed since it was explained by the expert (that is, the trainer). The user thus tends to adopt the wrong postures and to continue to do the exercise without even realizing the mistakes.

Thus, users of fitness equipment (both inside and outside gyms) have long felt the need to be able to do a workout correctly, optimizing the benefits of training and reducing the risks deriving from incorrect postures adopted during the performance of an exercise.

In light of this, several technical solutions are known for monitoring the way a movement is performed for fitness or orthopedic purposes.

For example, patent document EP0336030 describes a system for monitoring load lifting movement, comprising electromyographic sensors connected to the user's muscles and a sensor secured to the user's back in order to measure the angle of the user's back relative to the vertical.

The system also comprises a microprocessor connected to the sensors, a loudspeaker and a bar graph display unit connected to the microprocessor.

The bar graph display provides the user with feedback regarding the amount of force exerted by the muscles on which the sensors are positioned and the microprocessor activates the loudspeaker when the muscle force exerted exceeds predetermined thresholds.

The monitoring system described above is based on measuring predetermined physiological parameters associated with the movement of the user and comparing the measured values of the physiological parameters with preset thresholds.

This monitoring system, however, if used during the performance of a fitness exercise, would not be able to provide indications as to how to perform the exercise correctly, that is to say, corrective instructions that a trainer would provide. In effect, the system can only alert the user when the muscle force exerted exceeds predetermined levels or intensity.

Patent document U.S. Pat. No. 4,830,021 describes a monitoring system for locomotor activity, such as running and/or walking, comprising accelerometers, posture sensors and sensors for measuring the electrical activities of the heart, all secured to the user's body.

The monitoring system also comprises a unit which can record these signals and which can be secured to the user's body.

At the end of an exercise, the user can analyze the data on a computer.

This monitoring system does not therefore provide indications during the workout and, in light of this, at the end of the exercise, the user is not in a position to see whether or not the workout has been performed correctly.

Patent document EP0959956 in the name of Siemens relates to an orthopedic patient monitoring system comprising movement sensors associated with a part of the body and designed to measure pressure and shear forces and acceleration, a first memory for storing the information derived from the sensors, a second memory for a predetermined information model, a comparator for comparing the contents of the two memories and a device for displaying the result of the comparison.

The comparator is configured to compare the contents of the two memories only at the end of the exercise activity when all the information from the sensors is present in the first memory.

In light of this, that monitoring system is unsuitable for providing the type of indications on how to perform an exercise correctly that a trainer would provide.

In addition to the above, another drawback of the monitoring systems described above is that users are loath to wear sensors or monitoring devices.

Patent document U.S. Pat. No. 7,018,211 discloses a procedure for monitoring the performance of a free body exercise and which involves filming the user with a video camera.

That document, however, does not regard exercise machines for muscle power training.

Patent document US2009/131225A1 describes machinery for the rehabilitation of the arms and legs of users with motor disabilities or impairments.

That document, too, therefore, does not regard exercise machines for muscle power training. More specifically, the rehabilitation exercises performed with the machinery described in that document constrain the user's movements to specific postures and thus considerably limit freedom of movement.

Patent document U.S. Pat. No. 6,148,280 describes a system of sensors to be worn to assist a user in performing a movement with a golf club.

Thus, that document, too, does not regard exercise machines for muscle power training. Moreover, the sensors to be worn are uncomfortable for users.

Document WO2009/013679 describes dumb-bells or barbells used for performing fitness exercises and equipped with sensors to keep track of the movement performed by the user moving the dumb-bell or barbell so that, at the end of an exercise, the movement can be compared with a reference graph.

The solution described in that document does not, however, provide effective real-time assistance for a user performing an exercise with a muscle power exercise machine.

DISCLOSURE OF THE INVENTION

The aim of this invention is to provide an apparatus for the assisted performance of a fitness exercise using a muscle power exercise machine (in particular a functional machine) which overcomes the above mentioned drawbacks of the prior art and which meets the needs outlined above.

More specifically, the aim of this invention is to provide an apparatus for the assisted performance of a fitness exercise that allows the user to perform an exercise correctly, optimizing the beneficial effects associated with the exercise and reducing the risks deriving from incorrect postures that might be adopted during the performance of the exercise.

This aim is fully achieved by the apparatus for the assisted performance of a fitness exercise as characterized in the appended claims.

More specifically, the apparatus according to the invention is equipped with a fitness tool configured to interact with the user to enable the user to perform a movement along a preset path (or to maintain a predetermined position for a certain length of time corresponding to a physical strain) overcoming the force of a resistant load.

The term "fitness tool" is used to mean a "fitness machine".

According to the invention, the apparatus comprises, in combination:
    sensing means set up to provide a signal representing the movement of the user;
    feedback means for transmitting a signal to the user during performance of the exercise;
    a processor connected to the sensing means and to the feedback means to provide the user with feedback in real time on the correctness of performance of the exercise, based on a comparison between the signal representing the movement of the user and a predetermined reference pattern representing an ideal pattern for the movement of the user corresponding to the exercise performed correctly.

The fitness tool may comprise a resistant load and a mobile element connected to the resistant load and movable by the user along the preset path overcoming the resistant load.

More specifically, the apparatus according to the invention for the assisted performance of a fitness exercise is equipped with a fitness tool (configured to interact with a user to enable the user to perform a movement along a preset path overcoming the force of a resistant load), comprising:
    a frame;
    a weight stack movably associated with the frame to define the resistant load;
    at least one mobile element connected to the resistant load by a cable and movable by the user along a preset path overcoming the resistant load.

Preferably, in the fitness tool, the cable is trained around a plurality of pulleys and the mobile element comprises a handgrip associated with the cable, the fitness tool allowing the user to do a plurality of fitness exercises intended to train a plurality of the user's body muscles.

In this case, therefore, the fitness tool constitutes a "functional machine".

Alternatively, the fitness tool does not comprise a resistant load and the resistant load is constituted by a portion of the user's body when the user performs a movement of lifting/lowering that portion of the body overcoming the force of gravity acting on it. The fitness tool thus has a supporting and/or partially guiding function to allow the user to perform specific movements.

Advantageously, the apparatus proposed allows the user to be provided with feedback regarding the correctness of the exercise.

In effect, the sensing means derive a signal representing the user's movement which the processor compares with a reference pattern.

The processor sends the feedback to the user through the feedback means, that is to say, it provides the user with real-time feedback regarding the correctness of the exercise.

The user can thus obtain indications and/or information on how the exercise should be performed.

Further, thanks to these indications, the user can correct his or her movement if it is not correct.

The invention also provides an apparatus for assisting the user during the performance of a free body fitness exercise and which is as characterized in the appended claims.

More specifically, the apparatus comprises, in combination: sensing means set up to provide a signal representing the movement of the user and comprising a video camera for capturing images of the user during performance of the exercise; feedback means for transmitting a signal to the user during performance of the exercise and comprising a screen set up to display images; a processor connected to the sensing means and to the feedback means to provide the user with feedback in real time on the correctness of performance of the exercise, based on a comparison between the signal representing the movement of the user and a predetermined reference pattern representing an ideal pattern for the movement of the user corresponding to the exercise performed correctly.

The apparatus makes it possible to monitor free body movements whose kinematics, as is known, are very complex and characterized by many degrees of freedom.

As is known, in a free body exercise, there is no resistant load and the user performs the exercise by moving one part of the body relative to another.

The video camera films the user performing the free body exercise and provides a signal relating to the relative position of the user's body parts without the user having to wear any sensors.

The signal is compared by the processor with a reference pattern representing an ideal pattern for the user's movement and corresponding to the exercise performed correctly.

The processor sends the feedback to the user through the feedback means, that is to say, it provides the user with real-time feedback regarding the correctness of the exercise.

The user can thus obtain indications and/or information on how the free body fitness exercise should be performed.

Further, thanks to these indications, the user can correct his or her movement if it is not correct.

Advantageously, the apparatus proposed makes it possible to reduce the risks due to incorrect postures adopted while the exercise is being performed and to optimize the benefits associated with the exercise because the apparatus provides the user with real-time feedback showing the movement actually performed.

The aim is also achieved by a method for assisting a user in the performance of a fitness exercise as characterized in the appended claims.

In particular, the method is a method to assist a user in the performance of a fitness exercise, where the fitness exercise is performed using a fitness tool comprising a frame, a weight stack movably associated with the frame to define the resistant load, and at least one mobile element connected to the resistant load by a cable and movable by the user along a preset path overcoming the resistant load.

More specifically, the method is a method to assist a user in the performance of a fitness exercise, where the fitness exercise is performed using a fitness tool constituting a functional machine, in accordance with what is described above in connection with the apparatus.

According to the invention, the method comprises the following steps: sensing a signal representing the movement of the user when the user performs the fitness exercise; comparing in real time the signal representing the movement of the user with a preset reference pattern, representing an ideal pattern for the movement of the user corresponding to the fitness exercise performed correctly; transmitting to the user in real time a signal on the correctness of the performance of the exercise, according to the result of the comparison.

The method advantageously assists the user in the performance of an exercise using a fitness tool, whether comprising a resistant load or where the resistant load is constituted by a part of the user's body, or in the performance of free body exercises.

Advantageously, therefore, the method proposed allows a user to perform an exercise correctly even in the absence of a trainer. This is particularly advantageous for performing exercises without going to a gym.

It should be noted that the invention preferably contemplates setting a criterion for comparing how the exercise has actually been performed with how it should have been performed and a tolerance margin to determine, as a function of the comparison, whether the actual performance of the exercise differs from the ideal performance by an amount greater or smaller than the set tolerance margin.

In light of this, the invention contemplates displaying to the user an image representing the user's body and movements (user avatar) without at the same time displaying another image representing a body moving according to how the exercise should ideally be performed (avatar-trainer) until the actual performance differs from the ideal performance by an amount smaller than the preset tolerance margin.

According to the invention, the image representing the user's body and movements is displayed in an altered or modified manner so as to indicate on the image the mistake the user is making (in terms of difference from the ideal performance of the exercise) only when the real performance of the exercise differs from the ideal performance by an amount smaller than the preset tolerance margin.

Thus, the preset tolerance margin serves to provide the user with feedback, showing the mistake made and indicating the correct movement, only when the user's mistake exceeds the tolerance margin.

This advantageously avoids distracting the user's attention unnecessarily while he or she is performing the exercise.

This is particularly important when the user is performing an exercise that requires a great deal of concentration.

BRIEF DESCRIPTION OF THE DRAWINGS

These and other characteristics of the invention will become more apparent from the following detailed description of a preferred, non-limiting example embodiment of it, with reference to the accompanying drawings, in which:

FIGS. 3A and 3B are, respectively, a schematic rear view and a side view of yet another preferred embodiment of the apparatus for the assisted performance of a fitness exercise;

FIG. 4 is another schematic rear view of a further preferred embodiment of the apparatus according to this invention for the assisted performance of a fitness exercise;

FIG. 5 is a schematic rear view of an apparatus for assisting a user in the performance of a free body exercise, also according to the invention;

FIG. 8 schematically illustrates yet another mode of providing feedback for a user in a fitness machine according to the invention.

DESCRIPTION OF THE PREFERRED EMBODIMENTS OF THE INVENTION

Figure 1:
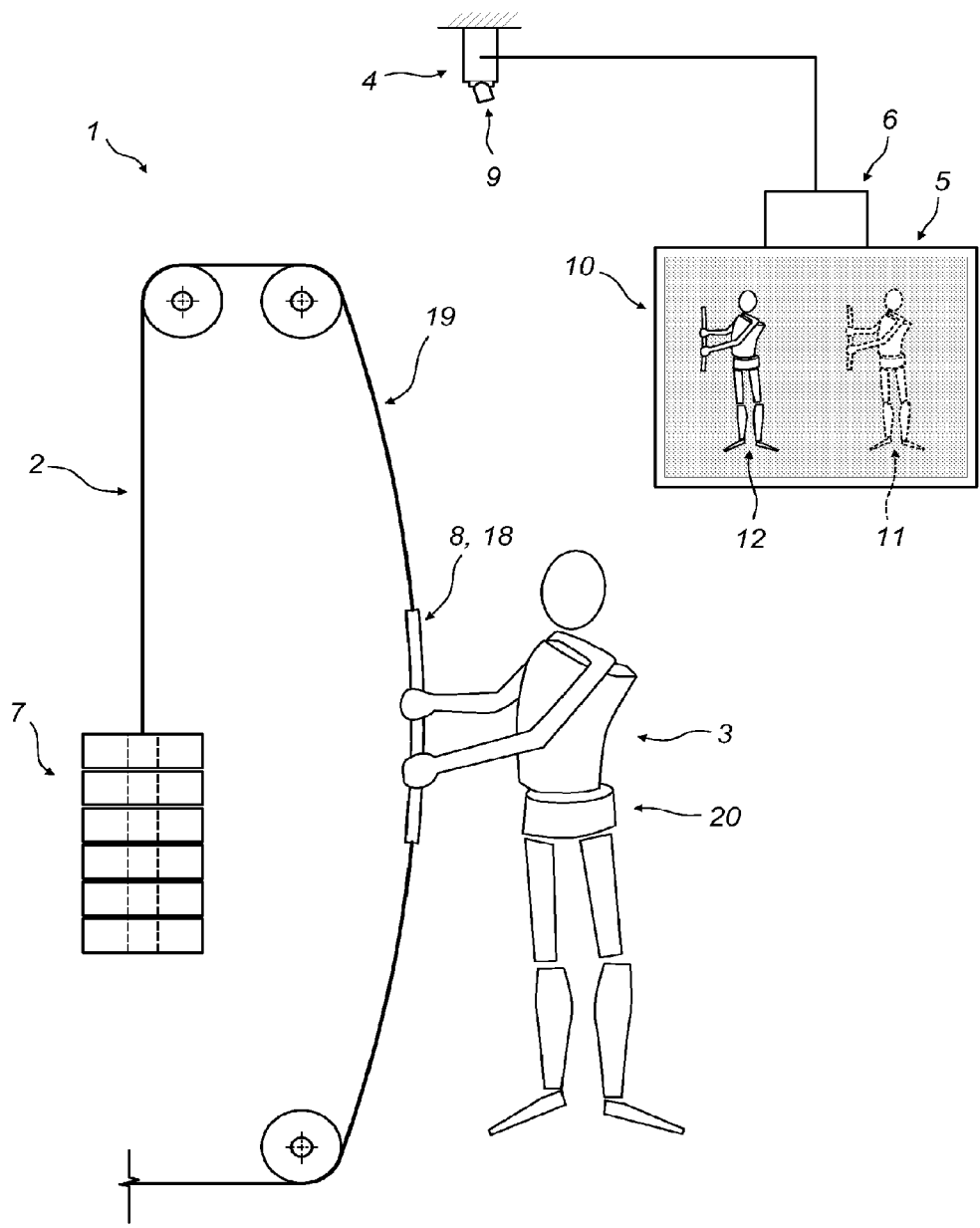
FIG. 1 is a schematic rear view of a preferred embodiment of the apparatus according to this invention for the assisted performance of a fitness exercise.

With reference to FIGS. 1 to 4, the reference numeral 1 denotes the apparatus according to the invention for the assisted performance of a fitness exercise, hereinafter also referred to as apparatus 1.

The term "user" denotes the person who performs an exercise using the apparatus of the invention.

Further, the expressions "correct exercise", "exercise performed correctly" and similar expressions are used herein to indicate a fitness exercise which has been performed according to a posture and/or a sequence of movements considered optimal by an expert in the field of physical education, or trainer.

In light of this, the term "movement" (referred to the feedback supplied by the apparatus) is used to denote the position adopted by the user's body during the performance of the exercise.

Generally speaking, during an exercise (at least during all dynamic fitness exercises, but excluding isometric exercises) some parts of the user's body are in movement relative to others.

Having said that, the term "movement" is used to denote the position adopted not only by the parts that should be moved during the exercise but also those that should be held still.

According to the invention, the apparatus 1 for the assisted performance of a fitness exercise comprises a fitness tool 2.

According to the invention, the fitness tool 2 is configured to interact with the user 3 to enable the latter to perform a movement along a preset path overcoming the force of a resistant load 7.

More specifically, the fitness tool 2 comprises:
- a frame (labeled 31 in FIGS. 3A and 3B and not illustrated in FIG. 1, but of per se known type);
- a weight stack movably associated with the frame to define the resistant load 7;
- at least one mobile element 8 connected to the resistant load 7 by a cable 19, 33 and movable by the user 3 along a preset path overcoming the resistant load 7.

Thus, the fitness tool 2 of FIG. 1 comprises a resistant load 7 and a mobile element 8 connected to the resistant load 7.

By way of a non-limiting example, the description below refers to a preferred embodiment of the apparatus 1 for the assisted performance of a fitness exercise, as illustrated in FIG. 1.

The mobile element 8 is a handgrip 18 associated with a cable 19 connected to the resistant load 7.

Preferably, the mobile element 8 is a handgrip 18 which is slidably associated with a cable 19 connected to the resistant load 7.

Alternatively, in variants not illustrated in the accompanying drawings, the mobile element 8 may be any constraining device connected to the cable 19, such as, for example, a strap.

To perform the fitness exercise, the user 3 moves the handgrip 18 along a predetermined path overcoming the force exerted by the resistant load 7 in response to the movement of the user 3.

The fitness tool 2 of FIG. 1 allows performance of a plurality of fitness exercises for training a plurality of muscles of the body 20 of the user 3 (for example, shoulders, chest, etc.). Thus, the fitness tool 2 constitutes (in the embodiment illustrated in FIG. 1) a functional machine.

More specifically, the cable 19 of the fitness tool 2 is trained around a plurality of pulleys and the mobile element 8 comprises a handgrip associated with the cable.

Thus, the fitness tool 2 allows the user 3 to perform a plurality of fitness exercises for training a plurality of muscles of the body of the user 3.

In this case, therefore, the fitness tool 2 constitutes a functional machine.

The apparatus 1 for the assisted performance of a fitness exercise comprises a video camera 9 configured to film the user 3 when performing the exercise.

The video camera 9 is configured to film a portion of, and preferably the entire, spatial volume in which the user 3 and/or the mobile element 8 moves/move during the performance of the exercise.

According to the invention, the video camera 9 constitutes sensing means 4 set up to provide a signal representing the movement of the user 3.

The apparatus 1 also comprises a screen 10 set up to display images.

By way of a non-limiting example, the screen 10 is an LCD screen.

Relative to the fitness tool 2 the screen 10 is positioned in such a way that the user 3 can observe the images displayed on it while performing the exercise.

According to the invention, the screen 10 constitutes feedback means 5 for transmitting a signal to the user 3 during performance of the exercise.

According to the invention, the apparatus 1 further comprises a processor 6 connected to the sensing means 4 and to the feedback means 5, that is to say, with reference to the non-limiting example embodiment of FIG. 1, to the video camera 9 and to the screen 10.

Also according to the invention, the processor 6 is configured to compare in real time the signal representing the movement of the user 3 with a preset reference pattern, representing an ideal pattern for the movement of the user corresponding to the fitness exercise performed correctly.

Preferably, the predetermined reference pattern is stored in the processor 6.

Below is a description of a preferred, non-limiting example mode of operation of the apparatus 1 of FIG. 1.

Other variants of the apparatus 1 of FIG. 1 will also be described below.

When the user 3 performs the fitness exercise by moving the handgrip 18 along the predetermined path, the video camera 9 captures images of the user 3.

Preferably, the processor 6 receives the images captured by the video camera 9 and drives the screen 10 in such a way that the latter displays the images captured by the video camera 9.

The screen 10 thus constitutes a sort of "mirror" in which the user can observe his or her own movement during performance of the exercise.

The image of the body 20 of the user 3 defines on the screen 10 a graphical element 12 representing the user.

The graphical element 12 is positioned on the screen 10 according to the actual position of the user 3. In effect, the position of the body 20 of the user 3 in the image displayed is correlated with the position actually adopted by the user 3 while performing the exercise.

The processor 6 is preferably configured to display on the screen 10 also a further graphical element 11, which is positioned according to the predetermined reference pattern.

Preferably, the further graphical element 11 is placed alongside, or alternatively superposed over, the graphical element 12.

The further graphical element 11 is a sort of "avatar trainer", or element representing the trainer in the images displayed on the screen 10.

The further graphical element 11, or "avatar trainer", preferably has the appearance of a human being.

The further graphical element 11 moves dynamically on the screen 10 and performs a correct movement, that is to say, it moves relative to the predetermined reference pattern.

In other words, while performing the exercise, the user 3 watches the screen 10 and observes both the movement of the graphical element 12 representing him or her, that is to say, of the image of his or her own body 20, and the movement of the further graphical element 11 representing the trainer or "avatar trainer", in order to ascertain whether or not his or her own movement during the exercise is a correct movement.

Advantageously, simply observing the images displayed on the screen 10 allows the user 3 to quickly and easily correct any mistakes he or she may be making in doing the exercise and thus provides the user 3 with real-time feedback regarding the correctness of the exercise being performed.

In addition, the apparatus 1 may also provide other useful information essential for performing a fitness exercise correctly.

For example, for many exercises, the user 3 must remain in a predetermined position for a predetermined length of time, usually a few seconds, in order to keep certain muscles contracted.

Further, when the user performs a plurality of these exercises consecutively, there is usually a pause between one exercise and the next, that is to say, a recovery time in which the muscles are not contracted.

According to this aspect of the invention, the processor 6 may also be configured to drive the feedback means 5 in such a way as to provide indications regarding the correct hold time for a predetermined position, and/or the correct recovery time between one exercise and another.

The expressions "correct hold time" and "correct recovery time" are used to mean the intervals of time an expert in the field of physical education would consider suitable for remaining in a specific position and for muscle recovery, respectively.

In a first variant of the apparatus 1 of FIG. 1 described above, the processor 6 is configured in such a way that the further graphical element 11, or "avatar-trainer", is positioned according to the predetermined reference pattern and also to the signal representing the movement of the user 3.

According to this variant, the further graphical element 11, or "avatar-trainer", moves on the screen 10 also relative to the position of the graphical element 12.

Advantageously, this allows the user 3 to have effective feedback on the correctness of the exercise irrespective of the speed at which he or she is doing the exercise. In effect, even if the user 3 is doing the exercise slowly, the movements of the further graphical element 11 on the screen 10 are coordinated with those of the graphical element 12, that is to say, the further graphical element 11 moves on the screen 10 and does the exercise correctly at substantially the same speed as the graphical element 12.

According to a second variant of the apparatus 1 of FIG. 1, the processor 6 is not configured to drive the screen 10 to display the images captured by the video camera 9.

According to this variant, the processor 6 is configured to derive from the images captured by the video camera 9 the position of the mobile element 8 and/or of the body 20 of the user 3, that is to say, to extract from the images captured by the video camera 9 a signal representing the position of the mobile element 8 and/or of the body 20 of the user 3.

Preferably, the processor 6 is furnished with an image analysis and recognition software.

By way of a non-limiting example, the processor 6 may be configured to recognize the barycenter of the mobile element 8 and/or the outline of the user's body 20.

The position of the mobile element 8 and/or of the body 20 of the user 3 defines the signal representing the movement of the user 3.

According to this variant, the processor 6 is configured to drive the screen 10 in such a way as to reproduce a graphical element 12 representing the movement of the user 3 and/or of the mobile element 8.

The graphical element 12 is a sort of "user avatar", that is, a graphical element representing the user 3 on the screen and/or the mobile element 8.

Preferably, the graphical element 12 has the appearance of a human being and/or of the mobile element 8.

The graphical element 12, like the one described above in connection with the preferred mode of operation of the apparatus 1 of FIG. 1, moves on the screen 10 relative to the movements of the user 3, that is to say, when the user makes a movement to perform the exercise, the graphical element 12 makes a corresponding movement on the screen 10.

According to this variant, the processor 6 is configured to display on the screen 10 the further graphical element 11 representing the trainer, that is to say, the "avatar-trainer", having the same technical features as the one described above with reference to the preferred mode of operation or the one of the first variant of the apparatus 1 of FIG. 1.

This second variant therefore differs from the embodiments of the apparatus 1 of FIG. 1 described above in that the graphical element 12 is not defined as an image of the body 20 of the user 3 but is a graphical element 12 generated by the processor 6.

Figure 2:
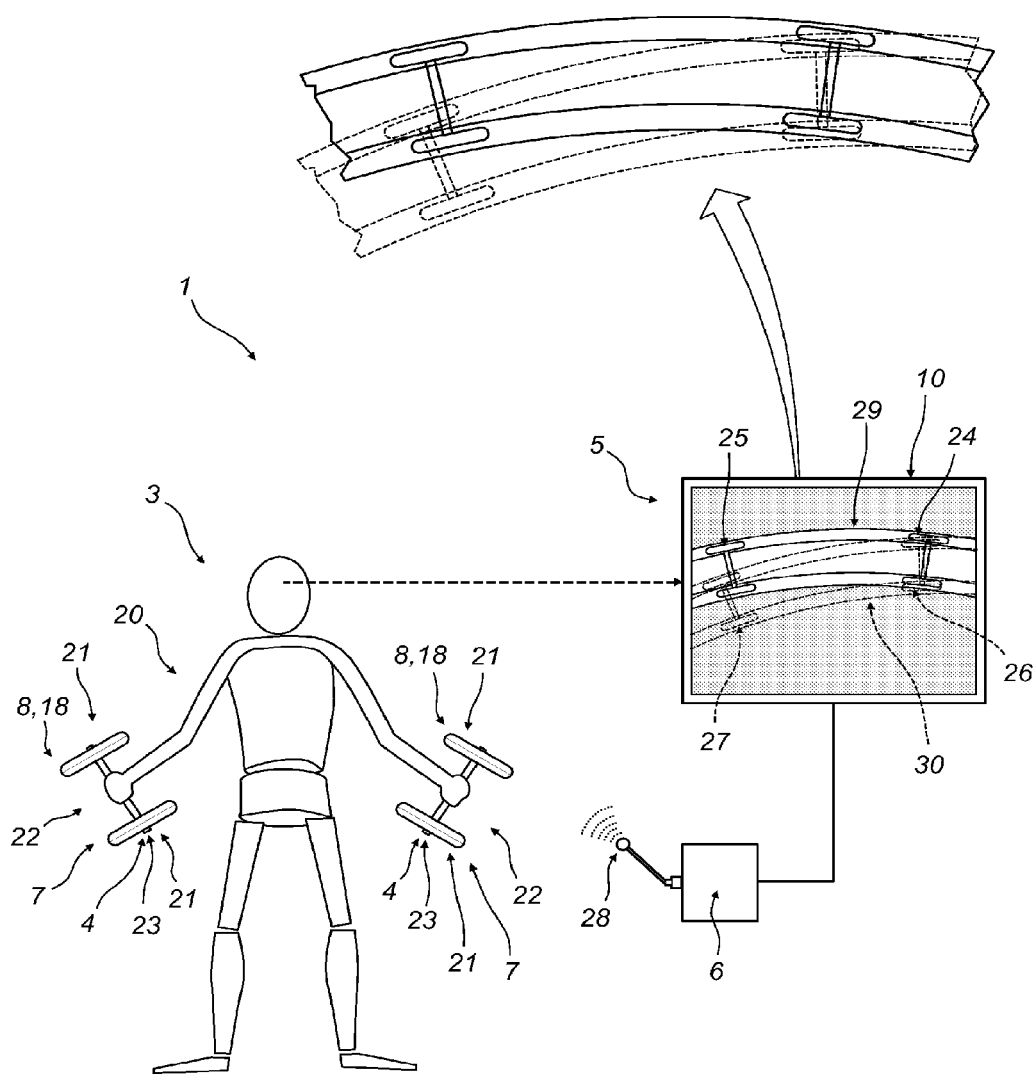
FIG. 2 is a schematic rear view of another preferred embodiment of the apparatus for the assisted performance of a fitness exercise.

By way of a non-limiting example, FIG. 2 illustrates another apparatus 1 for the assisted performance of a fitness exercise.

The apparatus 1 of the FIG. 2 comprises a fitness tool 2 having a resistant load 7 which defines a mobile element 8.

The fitness tool of FIG. 2 is a dumb-bell 22 having a handgrip 18 and a weight 21 at each end of the handgrip 18.

FIG. 2 illustrates a user 3 performing a fitness exercise with a pair of dumb-bells 22. More specifically, the user 3 holds a first dumb-bell 22 in the right hand and a second dumb-bell 22 in the left hand to perform an exercise consisting of moving the dumb-bells 22.

In this embodiment, the apparatus 1 comprises a position sensor 23 associated with each dumb-bell 22.

The position sensor 23 is configured to sense the position of the dumb-bell 22 it is associated with relative to a fixed spatial reference system.

The position sensor 23 of the dumb-bell 22 defines the sensing means 4.

Thus, the position sensors 23, that is, the sensing means 4, are set up to provide a signal representing the position of the dumb-bell 22.

The position sensors 23 are configured to transmit the dumb-bell 22 position signal to the processor 6 preferably through a wireless transmission system 28.

The apparatus 1 comprises a screen 10 set up to display images and defining the feedback means 5.

According to this variant, the ideal pattern for the movement of the user 3 comprises an ideal path for the dumb-bells 22 corresponding to the fitness exercise performed correctly.

The processor 6 is configured to compare the sensed signal of dumb-bell 22 position with the ideal path of the dumb-bells 22 corresponding to the fitness exercise performed correctly.

Below is a description of a preferred, non-limiting example mode of operation of the apparatus 1 of FIG. 2.

The user 3 performs the fitness exercise and the dumb-bell 22 position sensors 23 transmit the dumb-bell 22 position signal to the processor 6.

The processor 6 is configured to drive the screen 10 in such a way that dynamic images are displayed.

FIG. 2 illustrates the screen 10 on completion of the exercise.

On the screen 10, two graphical elements 24, 25, shown by the unbroken line, represent the actual positions of the dumb-bell at the beginning and end of the exercise, respectively, and two further graphical elements 26, 27, shown by the dashed line, represent the ideal positions of the dumb-bell at the beginning and end of the exercise, respectively, that is to say, the positions the dumb-bell would adopt if the exercise is performed correctly.

Also illustrated are two regions 29 corresponding to the actual path followed by the dumb-bell 22 during the exercise and two further regions 30 corresponding to the ideal path followed by the dumb-bell 22 during the exercise, that is to say, the path the dumb-bell would follow if the exercise is performed correctly.

At the end of and during the exercise, by simply observing the screen 10 which displays images representing the positions actually adopted and/or the paths actually followed by the dumb-bells 22 relative to the ideal positions and the ideal paths of the dumb-bells 22, the user 3 has immediate feedback regarding the correctness of the exercise he or she has just performed.

In effect, the image displayed on the screen 10 is updated in real time by the processor 6, which is set up to display on the screen some graphical references 24, 25, 29 as a function of the sensed position of the dumb-bells and other graphical references 26, 27, 30 as a function of the ideal path of the dumb-bells corresponding to the predetermined exercise performed correctly.

Advantageously, simply observing the images displayed on the screen 10 allows the user 3 to quickly and easily correct any mistakes he or she may be making in doing the exercise and thus provides the user 3 with real-time feedback regarding the correctness of the exercise being performed.

According to a variant of the apparatus of FIG. 2 not illustrated in the drawings, the sensing means 4 comprise a video camera designed to capture images of the user 3 performing the exercise.

According to this variant, the processor 6 is preferably configured to derive the position of the dumb-bells 22 from the images captured by the video camera.

By way of a non-limiting example, the processor 6 may be configured to recognize in the image the position of the barycenter of the weights 21 of the dumb-bells 22 and/or the outline of the dumb-bells 22.

This variant has the same advantageous technical features as those described above with reference to the apparatus 1 of FIG. 2 equipped with position sensors.

By way of a non-limiting example, FIGS. 3A and 3B illustrate another example of an apparatus 1 for the assisted performance of a fitness exercise.

The fitness tool 2 of FIGS. 3A and 3B is a tool known as a "lateral-machine", which comprises a frame 31, a plurality of pulleys 32, a cable 33 with a first end 34 and a second end 35 and trained around the pulleys 32, a mobile element 8 fixed to the first end 34 of the cable and a resistant load 7 fixed to the second end 35 of the cable.

The fitness tool 2 also comprises a seat 36 for the user 3.

The mobile element 8 comprises a bar 37 which the user 3 grips with both hands to perform the exercise.

With this type of fitness tool 2, the user 3 does fitness exercises by moving the bar 37 towards/away from his or her body 20 in a plane which is preferably vertical or, at most, slightly inclined.

Preferably, in this embodiment of the apparatus 1, the sensing means 4 comprise a plurality of optical barriers 13.

The optical barriers 13 comprise a light emitting device 39, that is, a device for emitting a light beam F, preferably collimated, and a receiving device 40 designed to receive a part of the emitted light.

Each optical barrier 13 thus provides a signal indicating the presence/absence of an opaque body positioned on the path of the light beam F between the light emitting device 39 and the receiving device 40, that is to say, a signal relating to the interruption of the light beam F between the light emitting device 39 and the receiving device 40.

The signal relating to the interruption of the light beam F defines a signal which represents the movement of the user 3 and which is used by the processor 6 to provide the feedback regarding the correctness of the exercise.

In effect, the processor 6 is configured to drive the feedback means 5 according to the light beam F interruption signal.

Preferably, the optical barriers 13 are positioned in such a way as to define two planes P1, P2, that is to say, a first, front plane P1 and a second, rear plane P2.

The planes P1, P2 delimit a spatial region R within which the user 3 must keep the bar 37 and his or her own body 20 in order to perform the exercise correctly.

Further, preferably, the sensing means 4 comprise an inclination sensor 41 designed to measure the inclination of the bar 37 in a vertical plane.

Preferably, the inclination sensor 41 is fixed to the bar 37.

The feedback means 5 comprise a screen 10 set up to display images.

The processor 6 is configured to display graphical references on the screen 10 according to the light beam F interruption signal.

By way of an example, the screen illustrated in FIG. 3A shows an image which comprises at the top of it a rectangular graphical reference 43, with which four arrow type graphical elements are associated, and at the bottom of it a circular graphical reference 44, with which another two arrow type graphical references are associated.

The rectangular graphical reference 43 schematically represents the bar 37 viewed from the back and the circular graphical reference 44 represents the same bar 37 viewed from the side.

The processor 6 is configured to activate the arrow graphical references according to the interruption signal sensed.

By way of a non-limiting example, interruption of one of the optical barriers 13 of the second, rear plane P2 causes the arrow labeled 45 to be activated. This provides the user with an indication as to how the movement can be corrected, that is to say, it tells the user that for the exercise to be done correctly, he or she must keep the bar 37 closer to the body, that is to say, further away from the plane P2.

Preferably, the processor 6 is also configured to display graphical references on the screen according to the signal from the inclination sensor 41.

By way of a non-limiting example, the processor 6 may be configured in such a way that when the inclination of the bar 37 in the vertical plane is not consistent with the predetermined reference pattern for the inclination, it activates on the screen the arrow graphical references labeled 46. This provides the user with an indication as to how the movement can be corrected, that is to say, it tells the user 3 that for the exercise to be done correctly, he or she must rotate the bar 37 in a vertical plane, as indicated by the arrow graphical references 46.

The feedback means 5 also comprise a device 42 for emitting colored light.

The processor is configured to drive the device 42 for emitting colored light in such a way that the device emits light of a certain color, for example green, when the processor 6 senses that the user 3 is doing the exercise correctly, and light of another color, for example red, when the processor 6 senses that the user 3 is not doing the exercise correctly.

FIG. 4 illustrates another embodiment of the proposed apparatus 1 for the assisted performance of a fitness exercise where the fitness tool 2 is a fitness tool 2 known in the trade as a "lower back bench".

The fitness tool 2 comprises a frame 47 equipped with a supporting member 48 designed to support the legs of the user 3 when he or she does the exercise and a securing device 49 for holding the body 20 of the user 3 against the frame 47, or rather, against the supporting member 48.

With this fitness tool 2, the user 3, after placing the legs on the supporting member 48 and securing the body 20 to the frame 47 using the securing device 49, does a fitness exercise consisting of lifting and lowering the trunk, that is to say, oscillating the torso about the waist.

This fitness tool 2 does not comprise a resistant load since the resistant load is constituted by the torso of the user 3 which the user 3 alternately lifts and lowers against the force of gravity acting on it.

The sensing means 4 of the apparatus of FIG. 4 comprise an optical barrier 13.

The optical barrier 13 comprises a light emitting device 39, that is, a device for emitting a light beam, preferably a low divergence beam, and a receiving device 40 configured to receive a part of the light emitted by the light emitting device 39.

The optical barrier 13 thus provides a signal indicating the presence/absence of an opaque body positioned on the path of the light beam F between the light emitting device 39 and the receiving device 40, that is to say, a signal relating to the interruption of the light beam F between the light emitting device 39 and the receiving device 40.

The signal relating to the interruption of the light beam F defines a signal which represents the movement of the user 3.

The optical barrier 13 is positioned in such a way that when the user 3 does the exercise correctly, the light beam F is not interrupted.

In effect, the user 3 interrupts the light beam F during the exercise if he or she is arching the back and thus making an incorrect movement.

In the example of FIG. 4, the optical barrier 13 is positioned in such a way that the path followed by the light beam F is a substantially horizontal path.

The feedback means 5 preferably comprise an acoustic warning device 14 designed to emit an audible warning.

The processor 6 is set up to activate the acoustic warning device 14 according to the light beam F interruption signal, that is to say, it activates the warning device if it senses that the light beam F has been interrupted.

Preferably, the apparatus 1 comprises a control element 16 configured to interact with the processor 6 in such a way that the processor 6 enables/disables the feedback and the transmission of the feedback to the feedback means 5.

The user 3 advantageously acts on the control element 16 to disable the feedback when the exercise is not being performed. This is particularly advantageous when the user is getting ready to start the exercise on the fitness tool because it prevents the emission of warning signals caused by inadvertent interruption of the optical barrier 13 before starting the exercise.

The apparatus 1 according to the invention for the assisted performance of a fitness exercise, illustrated in FIGS. 1 to 4 and described above, allows the user 3 to perform a fitness exercise correctly.

In effect, advantageously, the apparatus 1 provides real-time feedback regarding the correctness of the exercise being done and is also able to provide useful indications on how to correct the user's movement while the exercise is being done.

In other words, the apparatus 1 allows the user to optimize the benefits associated with an exercise being done (increase in muscle tone, power, etc.) and reduces the risks deriving from incorrect postures that might be adopted during the performance of the exercise.

Also, advantageously, the apparatus 1 for the assisted performance of a fitness exercise is configured in such a way that the user 3 does not have to wear any sensor. In effect, it is known that users of fitness equipment are reluctant to wear monitoring equipment and/or sensors.

FIG. 5 illustrates by way of a non-limiting example an apparatus 100 for assisting the user 3 in the performance of a free body fitness exercise, also according to the invention.

The apparatus 100, according to the invention, comprises a video camera 9 configured to film the user 3 performing the exercise.

The video camera 9 constitutes sensing means 4 set up to provide a signal representing the user 3.

Also according to the invention, the apparatus 100 further comprises a screen 10 set up to display images.

The screen 10 constitutes feedback means 5 for transmitting a signal to the user 3 during performance of the exercise.

The apparatus 100 further comprises a processor 6 connected to the sensing means 4 and to the feedback means 5 to provide the user with real-time feedback on the correctness of performance of the exercise, based on a comparison between the signal representing the movement of the user and a predetermined reference pattern representing an ideal pattern for the movement of the user corresponding to the exercise performed correctly.

Below is a description, with reference to FIG. 5, of a preferred, non-limiting example mode of operation of the apparatus 100 for assisting the user 3 in the performance of a free body fitness exercise.

Other variants of the apparatus 100 of FIG. 5 will also be described below by way of non-limiting examples.

FIG. 5 shows a user 3 doing a free body exercise and, more specifically, an exercise consisting of lifting and lowering the arms.

The video camera 9 of the apparatus 100 films the user 3 performing the fitness exercise.

Preferably, the processor 6 receives the images captured by the video camera 9 and drives the screen 10 in such a way that the latter displays the image of the body 20 of the user 3 captured by the video camera 9.

The screen 10 thus constitutes a sort of "mirror" in which the user can observe his or her own movement during performance of the exercise.

The image of the body 20 of the user 3 defines on the screen 10 a graphical element 12 representing the user.

The graphical element 12 is positioned on the screen 10 according to the movement of the user 3. In effect, the position of the body 20 of the user 3 in the image displayed is correlated with the position actually adopted by the user 3 while performing the exercise.

The processor 6 is preferably configured to display on the screen 10 also a further graphical element 11, which is positioned according to the predetermined reference pattern.

Preferably, the further graphical element 11 is placed alongside, or alternatively superposed over, the graphical element 12.

The further graphical element 11 is a sort of "avatar trainer", or element representing the trainer in the images on the screen 10.

The further graphical element 11, or "avatar trainer", preferably has the appearance of a human being.

The further graphical element 11 moves dynamically on the screen 10 relative to the ideal reference pattern stored and performs a correct fitness movement.

In other words, while performing the free body exercise, the user 3 watches the screen 10 and observes both the movement of the graphical element 12 representing him or her, that is to say, of the image of his or her own body 20, and the movement of the further graphical element 11 representing the trainer or "avatar trainer", in order to ascertain whether or not his or her own movement during the exercise is a correct movement.

Advantageously, simply observing the images displayed on the screen 10 allows the user 3 to quickly and easily correct any mistakes he or she may be making in doing the exercise and thus provides the user 3 with real-time feedback regarding the correctness of the exercise being performed.

In a first variant of the apparatus 100 of FIG. 5, the processor 6 is configured in such a way that the further graphical element 11 is positioned according to the predetermined reference pattern and also to the signal representing the movement of the user.

According to this variant, the further graphical element 11 moves on the screen 10 also relative to the position of the graphical element 12.

Advantageously, this allows the user 3 to have effective feedback on the correctness of the exercise irrespective of the speed at which he or she is doing the free body exercise. In effect, even if the user 3 is doing the exercise slowly, the movements of the further graphical element 11 on the screen 10 are coordinated with those of the graphical element 12, that is to say, the further graphical element 11 moves on the screen 10 and does the exercise correctly at substantially the same speed as the graphical element 12.

According to a second variant of the apparatus 100, the processor 6 is not configured to drive the screen 10 to display the images of the body 20 of the user 3 captured by the video camera 9.

According to this variant, the processor 6 is configured to derive from the images received the reciprocal position of parts of the user's body.

Preferably, the processor 6 is furnished with an image analysis and recognition software.

In other words, for example, the processor 6 may be set up to derive the position of the arms relative to the torso and/or to recognize the angle between the different articulated parts of each arm (forearms, wrists, etc.).

The relative position of the different parts of the body defines the signal representing the movement of the user.

According to this variant, the processor 6 is configured to drive the screen 10 in such a way as to reproduce a graphical element 12 representing the movement of the user 3.

The graphical element 12 is a sort of "user avatar", that is, a graphical element 12 which represents the user 3 on the screen 10.

Preferably, the graphical element 12 has the appearance of a human being.

The graphical element 12 moves on the screen 10 relative to the movements of the user 3, that is to say, when the user makes a movement, the graphical element 12 makes a corresponding movement on the screen 10.

According to this variant, the processor 6 is configured to display on the screen 10 the further graphical element 11 having the same technical features as the one described above with reference to the apparatus 100.

This variant is therefore characterized in that the graphical element 12 is not defined as an image of the body 20 of the user 3 but is a graphical element 12 generated on the screen 10 by the processor 6.

This variant, too, has the same advantageous technical features as those described above with reference to the preferred mode of operation of the apparatus 100 of FIG. 5.

According to another aspect of the invention, relating both to the apparatus 1 for the assisted performance of a fitness exercise and to the apparatus 100 for assisting the user 3 in the performance of a free body fitness exercise, the processor 6 is set up to store the signal representing the movement of the user 3 during the performance of the predetermined exercise under optimum conditions in order to set it as the reference pattern.

The expression "optimum conditions" means the conditions in which the exercise is performed correctly, that is to say, the conditions in which a person performs the exercise in a manner considered optimal, in terms of posture, speed and body arrangement, by an expert in the field of physical education.

In other words, the processor 6 is configured in such a way that it is possible to store the signal representing the movement of the user 3 in order to derive the reference pattern from it.

This advantageously allows the reference pattern to be saved quickly and easily.

Advantageously, the apparatus 100 proposed allows the user 3 to be assisted in performing free body exercises by providing indications useful for correcting the user's movement.

In other words, the apparatus 100 allows the user 3 to obtain indications regarding the correctness of the exercise performed, at a limited cost since it does not require the presence of specialist personnel such as a trainer.

The apparatus 100 proposed thus advantageously makes it possible to optimize the beneficial effects associated with the free body exercise and to reduce the risks deriving from incorrect postures that might be adopted during the performance of the exercise.

The different aspects of the apparatuses 1 and 100 described above can all be combined with each other, that is to say, the embodiments described above by way of non-limiting examples and the different aspects of each embodiment are not to be considered mutually exclusive.

In effect, the sensing means 4 may comprise a video camera, position sensors, an optical barrier and inclination sensors, in combination with, or alternatively to, each other.

In addition, the feedback means 5 may comprise a screen, a colored light emitting device and an acoustic warning device, in combination with, or alternatively to, each other.

Preferably, the fitness tool 2 comprises: a frame, a weight stack movably associated with the frame to define the resistant load 7; at least one mobile element 8 connected to the resistant load 7 by a cable 19, 33 and movable by the user 3 along a preset path overcoming the resistant load 7. It should be noted that according to the invention, the fitness tool 2 is a fitness machine.

Preferably, the fitness machine 2 is a functional training machine (of the type having the mobile element 8, or whose handgrip is inserted in a stretch of cable in fixed or slidable manner, or is connected to one end of the cable itself).

The sensing means 4 preferably comprise a three-dimensional movement sensor (such as, for example, a video camera and an infrared emitter) to sense signals relating to the user's position in space (sensed signals).

The apparatus according to the invention preferably also comprises a memory with a database containing data relating to the exercises to be performed.

In light of this, reference signals corresponding to a user performing the exercises correctly are stored for each of the exercises.

The correct movement is defined as a succession of correct positions alternated with predetermined time intervals.

Also stored in the memory, in addition to the reference positions, are the correct speed and magnitude data (reference speed and magnitude) of the movement, for each exercise.

It should be noted that correct performance of the exercise regards the following aspects of the exercise: the sequence of the movements (for example, correct movement of arms and legs), and the speed and magnitude of the user's movements.

The fitness machine according to the invention also comprises a processor 6 (that is, a central unit) which receives the signals sensed by the sensing means 4, processes them and compares them with the reference signals to identify any differences in terms of sequence, speed and/or magnitude of the movement, within a predetermined tolerance parameter.

Based on the signals sensed, the central unit 6, also builds an image of the user (from the position sensed) and generates a feedback signal on the correctness of the movement based on the previous comparison with the reference signals stored in the memory.

The central unit 6 compares the sensed position with the reference position and takes into account a predetermined position and speed tolerance.

More specifically, the central unit (that is, the processor 6) calculates the tolerance automatically as a function of the user's data (for example, age, body mass index and other user parameters, whether entered or sensed) or based on the performance of a predetermined movement (according to a calibration procedure where the user performs a predetermined movement from which the central unit 6 derives the tolerance).

For example, the tolerance may be implemented by programming the processor 6 in such a way that the various parts of the user's body (legs, arms, etc.) which are defined according to the reference signal, (that is, the positions of the parts of the user's body calculated at successive points in time based on the reference exercise representing its ideal performance) are considered by the processor as larger (by a preset factor) than the corresponding portions which are defined according to the sensed signal, so that the sensed position does not necessarily have to lie exactly over the reference position for the feedback signal to define an exercise as having been performed correctly (or at least to prevent the mistake from being indicated in real time on the graphical representation of the user).

Obviously, the predetermined tolerance value is correlated with the difficulty of the exercise.

With reference to the display means 10, preferably the display means of the fitness machine comprise a screen for displaying the images processed by the central unit 6.

These images, processed by the central unit 6, correspond to the feedback signal generated by the central unit 6 and displayed according to the methods described below.

Thus, displaying of the images on the screen constitutes the feedback telling the user whether or not the exercise is being performed correctly. In particular, it should be noted that this feedback is provided in real time.

Below is a description of the different feedback methods that may be implemented in the apparatus according to the invention (alternatively to, or in combination with, each other).

Figure 6:
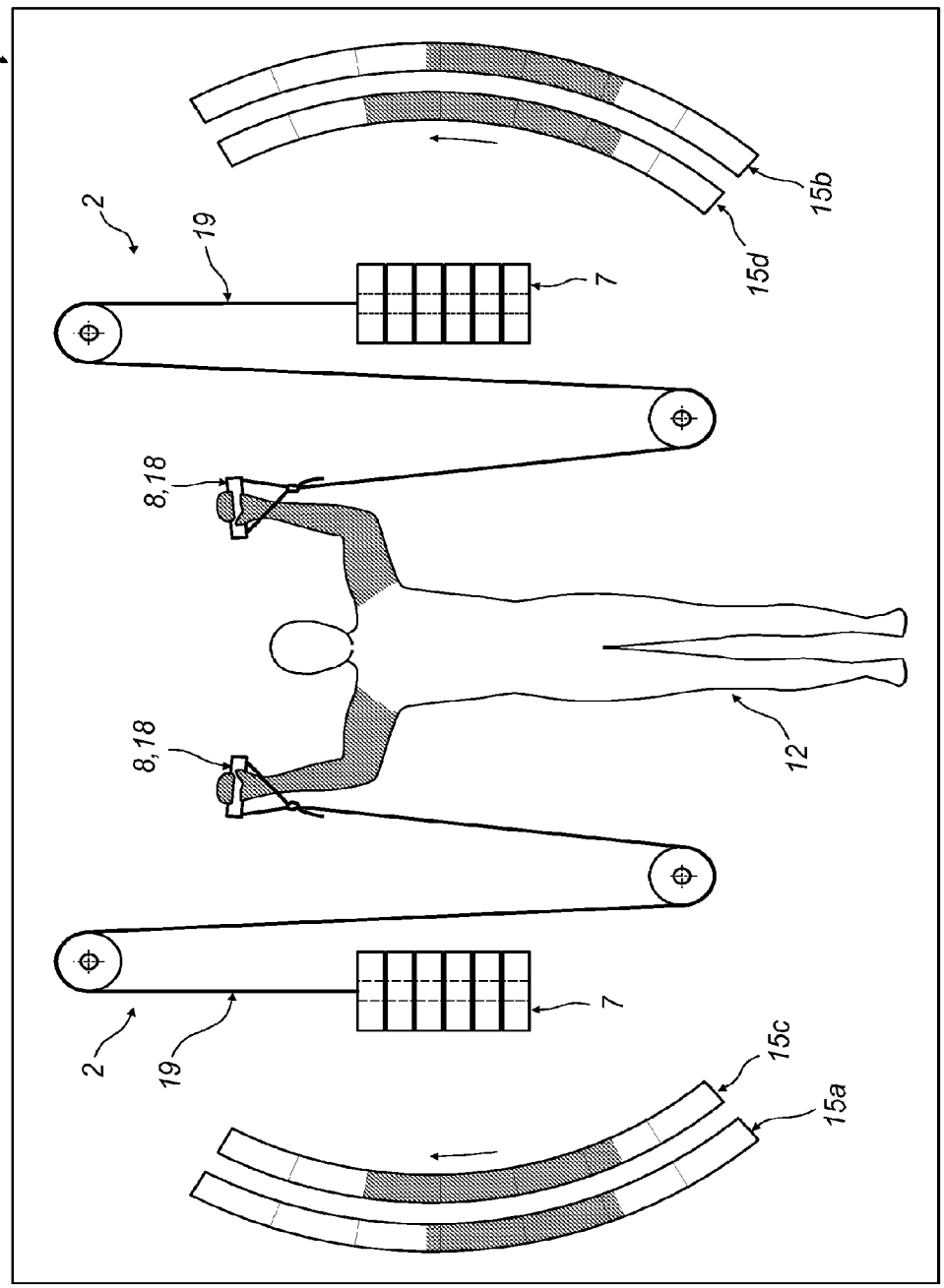
FIG. 6 schematically illustrates a mode of providing feedback for a user in a fitness machine according to the invention.

In a first method, illustrated in FIG. 6, referred to as "single display" method, the user sees on the screen 10 a single representation of his or her body generated by the succession of user positions.

This representation is generated by the central unit (that is, the processor 6) based on the signals from the sensing means (for example, by the video camera) and on the data in the memory in such a way as to follow the movements of the real user performing the exercise.

In that case, if the user does not perform the exercise correctly, the image changes color (for example, it turns red) in the portion corresponding to the part of the body that has performed the wrong movement. Otherwise, (if the difference between the real exercise actually performed and the ideal exercise as it should be performed remains below the tolerance margin) no part of the user's image changes color (or is subjected to other changes).

For example, if the user moves the right arm instead of the left arm during the exercise, the right arm turns red.

Or if the speed and/or magnitude of the movement of the user's left arm is/are too high compared to the reference, the left arm turns red.

The user is thus guided in the performance of the exercise, that is to say, is provided, through this display method, with an indication regarding the correctness of the exercise.

Further, to provide an even more precise reference for the exercise in terms of speed and magnitude of the movement, two lateral bars 15a and 15b are displayed beside the image of the user, one for the right side 15b and one for the left side 15a, which fill up progressively while the exercise is being performed.

The speed at which the bars are filled defines the correct speed of the movement, while the extent of the part filled represents the correct magnitude of the movement. Preferably, the bars 15a and 15b are curved in shape, since the ends of the arms move along an arcuate trajectory.

Alongside each of the bars 15a and 15b there may be a further bar 15c,15d which fills up according to the sensed movement of the user.

That way, there are two bars on each side (15a and 15c for the left-hand side and 15b and 15d for the right-hand side) for the user to compare precisely the correctness of his or her movements in terms of speed and magnitude.

FIG. 6 represents the feedback which the user is provided with (preferably on the screen 10) if he or she moves his or her arms too fast compared to the correct movement. As shown, the arms are displayed in a different color from the rest of the body.

In a further variant display method, the feedback provided by changing the color of the arms in the image regards the sequence of arm movements (for example, right arm lifted instead of left arm).

In that case, the processor 6 uses a parameter representing the rhythm of the exercise performed by the user.

According to this variant, if the user's movements are incorrect in terms of speed and/or magnitude, the image displayed on the screen 10 does not change—that is, feedback is not provided by changing color—but instead the processor 6 calculates and displays a score at the end of the exercise, taking into account the differences in the speed and magnitude of the user's movements from the correct parameters.

Described below is a second feedback method, illustrated in FIG. 7, which is alternative or additional to the method described above.

In this case, the central unit 6 processes the signals of the sensing means 4 and generates a representation, of the user, or "sensed" image, and, using the reference positions stored in the memory, the display means 10 display two superposed images, a sensed image and a reference image.

Figure 7:
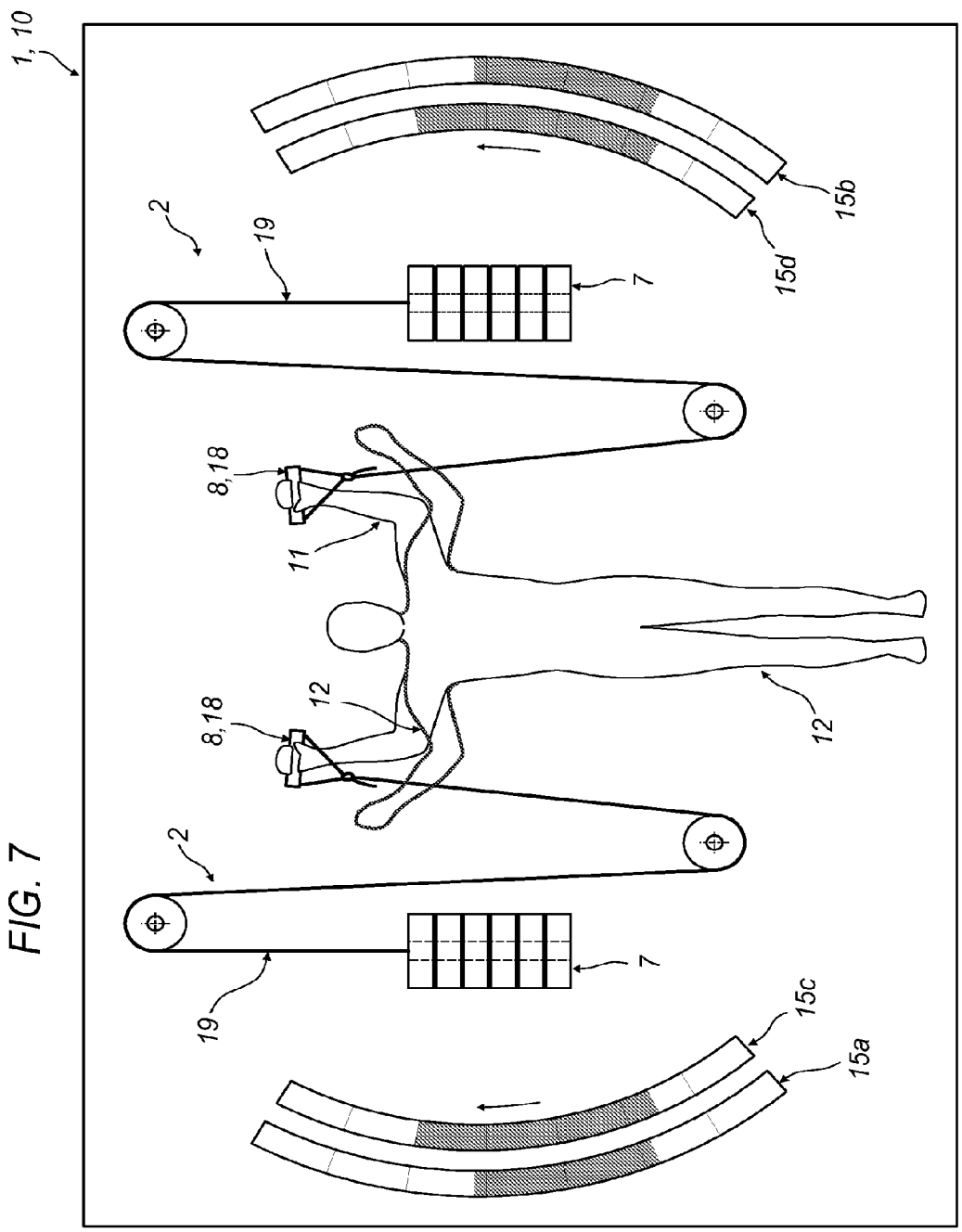
FIG. 7 schematically illustrates another mode of providing feedback for a user in a fitness machine according to the invention.

Thus, as shown in FIG. 7, two images are displayed on the screen 10 at any one time: one, labeled 12, is the sensed image and the other, labeled 11, is the reference image (derived by the processor 6) based on the data stored in the memory).

Thus, if the user performs the movement correctly in terms of sequence, speed and magnitude, only one image is displayed (corresponding to the two images, namely the reference image and the sensed image, "perfectly" superposed, whereas, if the user performs the movement incorrectly (again as a function of the preset tolerance margin), the image splits up at the part of the body which has performed the incorrect movement (for example, if the user lifts his or her right arm faster than the reference speed, the screen 10 displays an image with two right arms, one belonging to the reference image and one belonging to the sensed image whose arms are no longer superposed exactly over those of the reference image).

In this case, too, the lateral bars 15*a*, 15*b*, 15*c*, 15*d* are present to provide a reference for the speed and magnitude of the movement in the same way as described above.

FIG. 7 shows the feedback the user is provided with (that is, an image the user sees on the screen) if the arms are lifted faster than they should.

Described below is a yet another method of providing the user with feedback, illustrated in FIG. 8.

According to this feedback method, the representation of the user (image on the screen 10) is schematic and the user's arms and legs are represented by line segments.

In this case, too, the lateral bars 15*a*, 15*b*, 15*c*, 15*d* are present to provide a reference for the speed and magnitude of the movement (see method 1, above).

FIG. 8 shows the feedback the user is provided with (that is, the image displayed on the screen) if the arms are lifted faster than they should.

Whatever the case, irrespective of the method of displaying the error in performing the exercise (constituting real time feedback), the processor 6 is configured to calculate and display to the user at the end of the exercise information and data regarding how the exercise was actually performed as compared to how it should ideally have been performed (whether or not the difference between the real exercise and the ideal exercise exceeds the tolerance margin, thus constituting a comparative pattern for assessing the exercise.

It should be noted, therefore, that the apparatus according to the invention preferably contemplates the following.

The sensing means 4 are configured to sense a signal representing the position of the user performing the exercise. Preferably, the signal represents the position of the user in a succession of successive points in time (while he or she is performing the exercise).

For example, the sensing means 4 comprise a video camera 9 configured to film the user 3 during performance of the exercise. Alternatively (or additionally), the sensing means 4 comprise a three-dimensional movement sensor configured to sense the user's position and movement during the exercise.

Preferably, the feedback means 5 comprise a screen 10 for displaying images as a function of a drive signal generated by the processor 6.

The processor 6 is programmed to compare the sensed signal and the predetermined reference pattern based on the values adopted (in the successive points in time) by at least one predetermined assessment parameter representing an exercise pattern.

More specifically, the comparison is performed to calculate a difference between the value of the assessment parameter for the sensed signal and the corresponding value of the assessment parameter for the reference pattern. This difference is correlated with a reference quantity (predetermined and stored in the memory of the apparatus) to define a predetermined tolerance margin).

The processor 6 is programmed to generate the drive signal in such a way as to comprise, alternatively:
 a graphical representation of the user (the avatar 12) corresponding to the real position of the user and without the graphical elements based on the reference pattern if (or as long as) the difference (between the value of the assessment parameter for the sensed signal and the corresponding value of the assessment parameter for the reference pattern) is less than or equal to the predetermined tolerance margin; and
 a graphical representation of the user modified by graphical elements based on the reference pattern, to indicate the part of the body where the difference occurred, if the difference is greater than the predetermined tolerance margin.

Thus, the graphical representation of the user and the modified graphical representation of the user are not displayed simultaneously.

In effect, when the exercise is performed correctly (or acceptably according to the set tolerance) the unmodified graphical representation of the user is displayed (that is, the one with the user avatar only or, if there are two avatars, one the user avatar and the other the avatar trainer, the two are forcedly superposed, in the sense that the avatar trainer also moves according to the sensed signal and not according to the reference pattern), whereas when the exercise is performed incorrectly (or unacceptably according to the set tolerance), the modified graphical representation of the user is displayed where the user can clearly see the mistake made (by graphically altering the user avatar according to the reference pattern or by superimposing an avatar trainer or a part of an avatar trainer which moves according to the reference pattern).

Preferably, the processor 6 performs the comparison (between the sensed signal and the predetermined reference pattern) based on values adopted in the successive points in time starting from a first assessment parameter representing the position adopted by the user.

Preferably, the processor 6 performs the comparison (between the sensed signal and the predetermined reference pattern) also based on values adopted in the successive points in time starting from a second assessment parameter representing the speed of performance of the user's movements.

The tolerance margin may be set in such a way that the assessment of the two parameters is independent (it is sufficient for one of the two parameters to exceed the tolerance margin for the modified graphical representation of the user to be activated) or combined (both the parameters must exceed the respective tolerance margins, according to a predetermined criterion, to activate the modified graphical representation of the user).

Preferably, the modified graphical representation of the user comprises coloring or highlighting (on the graphical image representing the user's body, that is, on the user avatar 12) on the part of the body where the difference occurred (that is to say, the part of the body whose sensed position or speed of movement differs from the ideal pattern by an amount that exceeds the preset tolerance margin).

Alternatively, or additionally, the modified graphical representation of the user comprises graphical elements representing an ideal position of the user according to the reference pattern, in addition to the representation of the user, at least at the part of the user's body where the difference occurred.

Preferably, the processor is configured in such a way as to generate a drive signal according to the following.

Preferably, in addition to the graphical representation of the user (whether modified or unmodified), the drive signal comprises (that is, comprises information for the graphical displaying of) a right-hand filling bar 15c and a left-hand filling bar 15d, configured to visually indicate a state of forward movement and a speed of forward movement of the user's right and left hands, respectively.

In addition to the right and left filling bars 15c and 15d, the drive signal preferably further comprises (that is, further comprises information for the graphical displaying of) a right-hand reference filling bar 15a and a left-hand reference filling bar 15b, configured to visually indicate an ideal state of forward movement and an ideal speed of forward movement of the user's right and left hands, respectively, according to the reference pattern.

Further aspects of the invention are described below.

The sensing means 4 are set up to provide a signal representing the position of the mobile element 8.

In light of this, the ideal pattern for the movement of the user 3 comprises an ideal path of the mobile element corresponding to the fitness exercise performed correctly.

In one embodiment of the invention, the sensing means 4 comprise a video camera 9 configured to film the user 3 when performing the exercise, the graphical element 12 comprising a representation of the user filmed by the video camera 9, and where the processor 6 is programmed to display on the screen 10 another graphical element 11 according to the preset reference pattern and constituting the real-time feedback on the correctness of performance of the exercise.

In light of this, the processor 6 is programmed to display on the screen the other graphical element 11 as a function also on the signal representing the movement of the user 3.

In another embodiment of the invention, the sensing means 4 comprise at least one optical barrier 13 set up to generate a light beam F and to provide a signal indicating interruption of the light beam F, the processor 6 being programmed to activate the feedback means 5 according to the interruption signal.

In yet another embodiment of the invention, the feedback means 5 comprise an acoustic warning device 14.

In another embodiment of the invention, the feedback means 5 comprise a device 42 for emitting light which is colored according to the result of the comparison.

The apparatus 1 also comprises at least one control device 16 which may be operated by the user to switch the feedback means 5 off or on.

The description set out above also defines a method for assisting the user in the performance of a fitness exercise, comprising the following steps:
  sensing a signal representing the movement of the user 3 when the user 3 performs the fitness exercise;
  comparing in real time the signal representing the movement of the user with a preset reference pattern, representing an ideal pattern for the movement of the user 3 corresponding to the fitness exercise performed correctly;
  and transmitting to the user 3 in real time a signal on the correctness of the performance of the exercise, according to the result of the comparison.

Preferably, the step of sensing a signal representing the movement of the user 3 comprises capturing a signal representing the position of the body of the user 3 and/or of a mobile element 8 of a fitness tool 2 used by the user 3 to perform the exercise, and the ideal pattern for the movement of the user 3 comprises an ideal path for the body of the user 3 and/or for the mobile element 8 corresponding to the exercise performed correctly.

Preferably, the sensing step comprises capturing a sequence of images of the user 3.

Advantageously, the method proposed allows the user to be assisted in the performance of the fitness exercise in such a way as to provide real-time feedback which the user can use to correct the sequence of his or her movements. This allows the user to do the exercise correctly.

Preferably, the step of sensing (a signal representing the movement of the user 3) comprises capturing a signal representing the position and movement of the body 20 of the user 3.

In light of this, the ideal pattern for the movement of the user 3 comprises an ideal path (or temporal succession of positions) for the body 20 of the user 3.

Alternatively, or additionally, there is a step of capturing a signal representing the position and movement of a mobile element 8 of the fitness tool 2 (that is, of the fitness machine 2) used by the user 3 to perform the exercise.

In light of this, the ideal pattern for the movement of the user 3 comprises an ideal path (or temporal succession of positions) for the mobile element 8 corresponding to the exercise performed correctly.

The step of sensing a signal representing the movement of the user 3 comprises capturing a signal representing the position of the user in a succession of successive points in time while he or she is performing the exercise.

The sensing step is performed, for example, by capturing a sequence of images of the user or by means of data sensed by a three-dimensional movement sensor (whose operation is per se known).

Preferably, the comparison between the sensed signal and the predetermined reference pattern is based on the values adopted in the successive points in time by at least one predetermined assessment parameter representing an exercise pattern.

Preferably, the step of transmitting a signal comprises displaying images as a function of the comparison in such a way that the images comprise alternatively:
  a graphical representation of the user corresponding to the real position of the user and without the graphical elements based on the reference pattern if (or as long as) the difference between the value of the assessment parameter for the sensed signal and the corresponding value of the assessment parameter for the reference pattern is less than or equal to the predetermined tolerance margin; and
  a graphical representation of the user modified by graphical elements based on the reference pattern, to indicate the part of the body where the difference occurred, if the difference is greater than the predetermined tolerance margin.

Preferably, the comparison between the sensed signal and the predetermined reference pattern is performed as a function of a first assessment parameter, representing the position adopted by the user, and a second assessment parameter, representing a speed of the user's movements, by comparing the values adopted by the assessment parameters in the successive points in time for the sensed signal and corresponding values adopted by the assessment parameters in the successive points in time for the predetermined reference pattern.

As regards the use of the two assessment parameters in combination or in parallel, reference is made to the above description of the apparatus.

Preferably, the method comprises a step of processing the sensed signal and the reference pattern as a function of the comparison, in order to display a modified representation of the user comprising (alternatively or in combination):

coloring or highlighting on the part of the body where the difference exceeding the preset tolerance margin occurred;

graphical elements representing an ideal position of the user according to the reference pattern, in addition to (for example, partly superposed over) the graphical representation of the user, at least at the part of the user's body where the difference occurred.

Preferably, the method comprises displaying, in addition to the graphical representation of the user (whether modified or unmodified), a right-hand filling bar 15c and a left-hand filling bar 15d, configured to visually indicate a state of forward movement and a speed of forward movement of the user's right and left hands, respectively.

In addition (and possibly, alternatively) to the right and left filling bars 15c and 15d, the method comprises displaying a right-hand reference filling bar 15a and a left-hand reference filling bar 15b, configured to visually indicate an ideal state of forward movement and an ideal speed of forward movement of the user's right and left hands, respectively, according to the reference pattern.

Preferably, the filling bars are located (in the displayed image) on either side of the user representation 12.

Preferably, the filling bars are arcuate in shape.

The bars serve to provide the user with real time feedback on the correctness of the movement performed, giving him or her the chance, while doing the exercise, to see how the exercise should be performed (in terms of both position and movement speed, or rhythm).

It should be noted that the filling bars can be substituted by any other graphical element serving the same function such as, for example, a plurality of graphical elements that change color in temporal succession.

The fact that the bars are located at the sides of the user avatar 12 advantageously makes it possible not to distract the user.

Advantageously, therefore, the method proposed makes it possible to optimize the beneficial effects associated with the exercise and to reduce the risks deriving from incorrect postures that might be adopted during the performance of the exercise.

The invention described above is susceptible of industrial application and may be modified and adapted in several ways without thereby departing from the scope of the inventive concept. Moreover, all the details of the invention may be substituted by technically equivalent elements.

The invention claimed is:

1. An apparatus for the assisted performance of a fitness exercise, equipped with a fitness tool configured to interact with a user to enable the user to perform a movement along a preset path overcoming the force of a resistant load, the fitness tool comprising at least a dumb-bell having a handgrip provided with weights at its ends, wherein the apparatus comprises:

a detector configured to provide a signal representing the movement of the user;

a feedback generator for transmitting a feedback signal to the user during performance of the exercise;

a processor connected to the detector and to the feedback generator to provide the user with feedback in real time on the correctness of performance of the exercise, based on a comparison between the signal representing the movement of the user and a predetermined reference pattern representing an ideal pattern for the movement of the user corresponding to the exercise performed correctly, wherein the feedback generator comprise (i) a graphical representation of the body of the user generated by a succession of user positions and (ii) graphical elements based on the reference pattern and representative of the difference between the signal representing the movement of the user and the predetermined reference pattern, wherein the processor is programmed to display said graphical elements only when the difference between the signal representing the movement of the user and the predetermined reference pattern exceeds a predetermined tolerance margin, whereby the reference pattern is not displayed as long as the difference between the signal representing the movement of the user and the predetermined reference pattern is less than or equal to said predetermined tolerance margin.

2. The apparatus according to claim 1, wherein the detector is a video camera and the processor is configured to derive a position of the dumb-bell from images captured by the video camera.

3. The apparatus according to claim 1, wherein:

the detector is configured to sense a signal representing the position of the user performing the exercise in a succession of successive points in time;

the feedback generator comprises a screen for displaying images as a function of a drive signal generated by the processor;

the processor is programmed to compare the sensed signal and the predetermined reference pattern based on the values adopted in the successive points in time by at least one predetermined assessment parameter representing an exercise pattern, the processor being programmed to generate the drive signal in such a way that it comprises a graphical representation of the user corresponding to the real position of the user and without graphical elements based on the reference pattern if the difference between the value of the assessment parameter for the sensed signal and the corresponding value of the assessment parameter for the reference pattern is less than or equal to a predetermined tolerance margin; and a graphical representation of the user modified by graphical elements based on the reference pattern, to indicate the part of the body where the difference occurred, if the difference is greater than the predetermined tolerance margin.

4. The apparatus according to claim 3, wherein the processor is programmed to compare the sensed signal with the predetermined reference pattern as a function of the values adopted in the successive points in time by a first assessment parameter, representing the position adopted by the user, and by a second assessment parameter, representing a speed at which the user performs the movements.

5. The apparatus according to claim 3, wherein the modified representation of the user comprises coloring or highlighting on the part of the body where the difference occurred.

6. The apparatus according to claim 3, wherein the modified graphical representation of the user comprises graphical elements representing an ideal position of the user according to the reference pattern, in addition to the representation of the user, at least at the part of the user's body where the difference occurred.

7. The apparatus according to claim 3, wherein the drive signal comprises a right-hand filling bar and a left-hand filling bar, configured to visually indicate a state of forward movement and a speed of forward movement of the user's right and left hands, respectively.

8. The apparatus according to claim 7, wherein the drive signal further comprises a right-hand reference filling bar and a left-hand reference filling bar, configured to visually indicate an ideal state of forward movement and an ideal speed of forward movement of the user's right and left hands, respectively, according to the reference pattern.

9. The apparatus according to claim 1, wherein the detector comprises a video camera configured to film the user during performance of the exercise or a three-dimensional movement sensor configured to sense the user's position and movement during the exercise.

10. The apparatus according to claim 1, wherein the processor is set up to store the signal representing the movement of the user corresponding to the fitness exercise performed in an optimum manner, to set it as the reference pattern.

11. A method to assist a user in the performance of a fitness exercise using a fitness tool comprising at least a dumb-bell having a handgrip provided with weights at its ends,
wherein the method comprises the following steps:
sensing through a detector a signal representing the movement of the user when the user performs the fitness exercise through the fitness tool;
comparing in real time the signal representing the movement of the user with a preset reference pattern, representing an ideal pattern for the movement of the user corresponding to the fitness exercise performed correctly, wherein said comparison is carried out by a processor connected to the detector and to a feedback generator;
transmitting to the user in real time a signal on the correctness of the performance of the exercise, according to the result of the comparison, wherein said signal is transmitted through the feedback generator,
wherein said signal transmitted in real time to the user comprises: (i) a graphical representation of the body of the user generated by a succession of user positions and (ii) graphical elements based on the preset reference pattern and representative of the difference between the signal representing the movement of the user and the preset reference pattern,
wherein said graphical elements are transmitted to the user only when the difference between the signal representing the movement of the user and the predetermined reference pattern exceeds a predetermined tolerance margin, whereby no reference pattern is displayed as long as the difference between the signal representing the movement of the user and the predetermined reference pattern is above said predetermined tolerance margin.

12. The method according to claim 11, wherein
the step of sensing a signal representing the movement of the user comprises capturing a signal representing the position of the user in a succession of successive points in time while he or she is performing the exercise,
the comparison between the sensed signal and the predetermined reference pattern is based on the values adopted in the successive points in time by at least one predetermined assessment parameter representing an exercise pattern,
the step of transmitting a signal comprises displaying images as a function of the comparison in such a way that the images comprise
a graphical representation of the user corresponding to the real position of the user and without graphical elements based on the reference pattern if (or as long as) the difference between the value of the assessment parameter for the sensed signal and the corresponding value of the assessment parameter for the reference pattern is less than or equal to the predetermined tolerance margin, and
a graphical representation of the user modified by graphical elements based on the reference pattern, to indicate the part of the body where the difference occurred, if the difference is greater than the predetermined tolerance margin.

13. The method according to claim 12, wherein the comparison between the sensed signal and the predetermined reference pattern is performed as a function of a first assessment parameter, representing the position adopted by the user, and a second assessment parameter, representing a speed of the user's movements, by comparing the values adopted by the assessment parameters in the successive points in time for the sensed signal and corresponding values adopted by the assessment parameters in the successive points in time for the predetermined reference pattern.

14. The method according to claim 12, comprising a step of processing the sensed signal and the reference pattern as a function of the comparison, in order to display a modified representation of the user comprising:
coloring or highlighting on the part of the body where the difference exceeding the preset tolerance margin occurred;
graphical elements representing an ideal position of the user according to the reference pattern, substantially superposed over the graphical representation of the user at least at the part of the user's body where the difference occurred.

15. The method according to claim 12, comprising displaying, in addition to the graphical representation of the user,
a right-hand filling bar and a left-hand filling bar, configured to visually indicate a state of forward movement and a speed of forward movement of the user's right and left hands, respectively, and/or
a right-hand reference filling bar and a left-hand reference filling bar configured to visually indicate an ideal state of forward movement and an ideal speed of forward movement of the user's right and left hands, respectively, according to the reference pattern.

16. The apparatus according to claim 2, wherein the processor is configured to recognize in said image a position of a barycenter of the weights of the dumb-bell and/or an outline of the dumb-bell.

17. The apparatus according to claim 1, wherein the processor is configured to derive a position of the dumb-bell from the signal provided by the detector.

* * * * *